United States Patent [19]

Telschow

[11] Patent Number: 5,300,686
[45] Date of Patent: Apr. 5, 1994

[54] SELECTIVE REACTION OF TRIALKYLALUMINUM WITH ORGANOPHOSPHORUS DIHALIDE

[75] Inventor: Jeffrey E. Telschow, Tarrytown, N.Y.

[73] Assignee: Akzo nv, Arnhem, Netherlands

[21] Appl. No.: 467,711

[22] Filed: Jan. 19, 1990

[51] Int. Cl.$^5$ ................................................ C07F 9/02
[52] U.S. Cl. ...................................... 564/15; 564/16; 568/14; 568/17
[58] Field of Search ................. 564/15, 16; 568/14, 568/17

[56] References Cited

U.S. PATENT DOCUMENTS 3,036,132  5/1962  Becker .............................. 260/606.5

OTHER PUBLICATIONS

Okhlobystin et al, Bulletin of the Academy of Sciences pp. 977–979 (1958).

*Primary Examiner*—Thurman K. Page
*Assistant Examiner*—Jyothsna Venkat
*Attorney, Agent, or Firm*—Richard P. Fennelly; Louis A. Morris

[57] ABSTRACT

Organophosphorus dihalides can have one of their halogen substituents substituted with an alkyl group from a trialkylaluminum by gradual addition of the latter reagent to the former.

1 Claim, No Drawings

SELECTIVE REACTION OF TRIALKYLALUMINUM WITH ORGANOPHOSPHORUS DIHALIDE

BACKGROUND OF THE INVENTION

1. Field of the Invention

The present process relates to the selective reaction of a trialkylaluminum compound with an organophosphorus dihalide to yield a halodiorganophosphine.

2. Description of the Prior Art

It is known to react trialkylaluminum compounds with phosphorus trichloride to yield various substitution products depending on the conditions used. See Chemical Abstracts, Vol. 53, 1122f (1959).

More recently, it has been disclosed that compounds of the formula $RPCl_2$ (R being alkyl or aryl) can be alkylated with Grignard reagents (R'MgX) to form compounds of the formula RR'PCl. See Chemical Abstracts, Vol. 107, 77926s. However, the selectivity of these reactions is usually poor and mixtures result.

U.S. Pat. No. 3,036,132 to S. B. Becker has a general description of a metathesis reaction between (1) a phosphorus-halogen compound which is said to be of the formula $PR_nX_{3-n}$, where R can be a monovalent hydrocarbon radical and n can be 1 or 2 and (2) a compound of the formula $AlR_3$ or $M(AlR_4)_n$ where R can be as described above, M can be alkali metal or alkaline earth metal, and n is the valence of M. This patent indicates that control of the ratio of equivalents of either reactant will control the extent of hydrocarbon substitution in the phosphorus compound. At Col. 4, lines 5-9, however, it indicates that its "specific examples" illustrate how "the reactions can be controlled to yield intermediate products of hydrocarbon substitution into the phosphorus-halogen reactants". The Examples contained in this patent only use lithium aluminum tetrapropyl with phosphorus trichloride. No examples or more specific disclosure using the less reactive trialkylaluminum and an organophosphorus dihalide are given. U.S. Pat. Nos. 3,974,217 to J. A. Miles (at Col. 1, lines 23-27) and 4,810,425 to G. E. Nelson (at Col. 1, lines 27-29) discuss the Becker '132 patent solely in terms of relating to use of the more reactive $M(AlR_4)_n$ compounds as a reagent with either phosphorus trichloride or phosphorus tribromide.

SUMMARY OF THE INVENTION

The invention, in its broadest context, relates to the manufacture of halodiorganophosphines by the selective reaction of an organophosphorus dihalide with a trialkylaluminum compound.

DETAILED DESCRIPTION OF THE INVENTION

The instant invention is practiced by reacting a trialkylaluminum compound with an organophosphorus dihalide to selectively replace one of the halogen atoms on the organophosphorus dihalide with one of the alkyl groups of the trialkylaluminum. The reaction may be depicted by the following general formula:

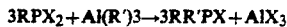

$$3RPX_2 + Al(R')_3 \rightarrow 3RR'PX + AlX_3$$

where R is organo (such as aryl, alkyl, and the like), R' is alkyl, and X is halo (such as chloro).

The organophosphorus dihalide which is one of the starting materials in the instant process preferably is benzene phosphorus dichloride (R being phenyl and X being chloro).

The trialkylaluminum compound used is one which contains alkyl groups (either straight or branched) of from 1 to about 12 carbon atoms. A preferred trialkylaluminum compound is trioctylaluminum which can be used to make octylphenylphosphine oxide which is a key intermediate in the synthesis of the transuranium extractant N,N-bis(2-methylpropyl)-2-(octylphenylphosphinyl) acetamide. In such a procedure the halodiorganophosphine is hydrolyzed to a secondary phosphine oxide for reaction with an N,N-dialkylcarbamoylmethyl halide.

The instant process can be suitably practiced by the slow, dropwise addition of the trialkylaluminum compound to the organophosphorus dihalide, which can either be neat or be dissolved in an organic solvent (e.g., a hydrocarbon solvent such as toluene). The reaction is conducted at temperatures of from about −20° C. to about 100° C. Preferably, the reaction is begun at a low temperature and is completed at a higher temperature.

The following Examples further illustrate the invention.

EXAMPLE 1

Benzene phosphorus dichloride (37.5 ml, 49.2 gm, 270 mmoles) was added to a 250 ml four-neck flask, under nitrogen atmosphere, with a mechanical stirrer. Neat trioctylaluminum (44 ml, 36.6 gm, 91.8 mmoles) was added slowly dropwise at 20°-30° C. using a cold water bath to cool the exotherm. The addition took one hour, and the resulting pale grey solution was heated to 30° C. for 3.5 hours and then 50° C. for twenty-three hours. Roughly 10% of the benzene phosphorus dichloride remained unreacted as indicated by gas chromatographic analysis.

The clear solution that resulted was cooled, diluted with 70 ml of toluene, and was treated with a solution of 51.0 gm (0.65 mole) of 51% sodium hydroxide in 30 ml of water at 10°-40° C. The mixture separated into layers after standing, and the toluene phase was washed three times with 25 ml of water. Evaporation of the toluene left 58.0 gm (90.1% yield) of a colorless liquid. Gas chromatographic analysis of this intermediate showed 93.2 area % octylphenylphosphine oxide and 5.7 area % of dioctylphenylphosphine oxide formed by oxidation of the corresponding phosphine by-product.

EXAMPLE 2

A 26.2 gm (0.10 mole) portion of the 91% octylphenylphosphine oxide from Example 1 was combined with 20.6 gm (0.10 mole of N,N-diisobutylchloroacetamide, 70 ml of toluene, 10 ml of water, 8.6 gm (0.11 mole) of 51% sodium hydroxide, and 60 mg of tetrabutylammonium chloride in a 250 ml three neck flask. The mixture was stirred rapidly at 50° C. for twenty hours and then at 70° C. for three hours. The cooled mixture was separated and the toluene layer was washed with dilute sodium chloride until the washings were no longer base. The toluene was stripped, and the residue was taken up in hexane, was filtered through CELITE filter medium, and was stripped of solvent again. The clear yellow oil weighed 41.1 gm (a quantitative yield) and showed 92 area % purity of N,N-bis(2-methylpropyl)-2-(octylphenylphosphinyl) acetamide by gas chromatographic analysis.

The foregoing Examples are provided for illustrative reasons and should not therefore be construed in a limiting sense. The scope of protection sought is set forth in the claims which follow.

I claim:

1. A process for the manufacture of N,N-bis(2-methylpropyl)-2-octylphenyphosphinyl)acetamide which comprises the manufacture of a composition comprising hydrolyzable halodiorganophosphine of the formula RR'PX, where R is phenyl, R' is octyl, and X is halo which comprises the selective reaction of an organophosphorus dihalide of the formula $RPX_2$ with a trialkylaluminum of the formula $Al(R')_3$, the hydrolysis of the halodiorganophosphine to octylphenylphosphine oxide, and the reaction of the octylphenylphosphine oxide with diisobutylchloroacetamide.

* * * * *